US00PP27540P3

(12) United States Plant Patent
Danziger

(10) Patent No.: US PP27,540 P3
(45) Date of Patent: Jan. 10, 2017

(54) ***PORTULACA* PLANT NAMED 'DPAZFCHSIA'**

(50) Latin Name: *Portulaca oleracea*
Varietal Denomination: DPAZFCHSIA

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 82 days.

(21) Appl. No.: 14/544,979

(22) Filed: Mar. 12, 2015

(65) Prior Publication Data

US 2016/0278272 P1 Sep. 22, 2016

(51) Int. Cl.
*A01H 5/02* (2006.01)

(52) U.S. Cl.
USPC ..... Plt./471

(58) Field of Classification Search
USPC ..... Plt./471
See application file for complete search history.

*Primary Examiner* — Susan McCormick Ewoldt
(74) *Attorney, Agent, or Firm* — Cassandra Bright

(57) ABSTRACT

A new and distinct *Portulaca* cultivar named 'DPAZFCHSIA' is disclosed, characterized by stable flower color, long blooming period—from Spring to Autumn, compact and semi-trailing habit. The new variety is a *Portulaca*, normally produced as an outdoor garden or container plant.

2 Drawing Sheets

Figure 1:
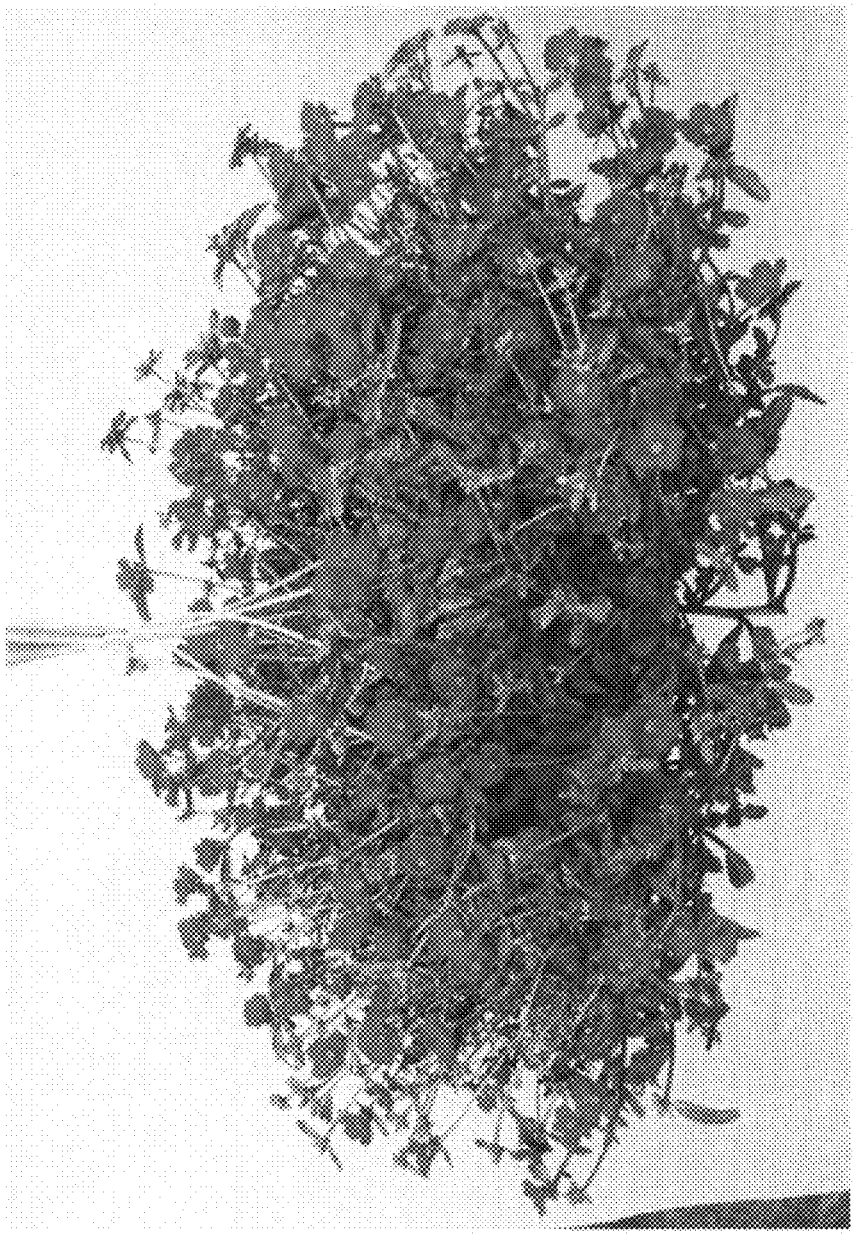

Latin name of the genus and species: *Portulaca oleracea.*
Variety denomination: 'DPAZFCHSIA'.

BACKGROUND OF THE INVENTION

The new *Portulaca* cultivar is a product of a planned breeding program conducted by the inventor, Gavriel Danziger, in Moshav Mishmar Hashiva, Israel. The objective of the breeding program was to produce new *Portulaca* varieties for ornamental commercial applications. The open pollination resulting in this new variety was made during 2010.

The seed parent is the, unpatented, proprietary variety referred to as *Portulaca* 'PT-9-650'. The pollen parent is unknown as it was an open pollination breeding program. The new variety was discovered in June of 2011 by the inventor in a group of seedlings resulting from the 2010 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in August of 2011 and has shown that the unique features of this cultivar are stable and reproduced true to type in more than 10 successive generations.

SUMMARY OF THE INVENTION

The cultivar 'DPAZFCHSIA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DPAZFCHSIA' These characteristics in combination distinguish 'DPAZFCHSIA' as a new and distinct *Portulaca* cultivar:

1. Compact and semi-trailing plant habit.
2. Vivid and stable flower color.
3. Long blooming period, from Spring to Autumn.

Plants of the new cultivar 'DPAZFCHSIA' are similar to plants of the seed parent, *Portulaca* 'PT-9-650' in most horticultural characteristics, however, plants of the new cultivar 'DPAZFCHSIA' differ in the following;

1. New variety has a more compact and denser habit.
2. Less trailing habit than seed parent.
3. New variety produces larger flowers.

COMMERCIAL COMPARISON

Plants of the new cultivar 'DPAZFCHSIA' are comparable to the commercial variety *Portulaca* 'Cupcakes Grape Jelly'. The two *Portulaca* varieties are similar in most horticultural characteristics; however, the new variety 'DPAZFCHSIA' differs in the following:

1. Leaves or the new variety are narrower in the apex and thinner overall.
2. Petal apex of the new variety is rounded while the petal apex of 'Cupcakes Grape Jelly' is retuse.
3. 'DPAZFCHSIA' has a plant habit which is semi trailing habit while the plant habit of 'Cupcakes Grape Jelly' is semi-upright.

Plants of the new cultivar 'DPAZFCHSIA' can also be comparable to the patented commercial variety *Portulaca* 'SAKPOR001' U.S. Plant Pat. No. 24,528. The two *Portulaca* varieties are similar in most horticultural characteristics; however, the new variety 'DPAZFCHSIA' differs in the following:

1. Flowers are different shade of purple; N74B while the 'SAKPOR001' flower color is 67A.
2. The new variety has a plant habit which is compact and semi-trailing; this comparator has a plant habit is semi-mounding and upright.

3. Plant vigor of the new variety is moderate; this comparator has a vigorous growth habit.

BRIEF DESCRIPTION OF THE PHOTOGRAPHS

The accompanying photograph in FIG. 1 illustrates in full color a typical plant of 'DPAZFCHSIA' grown in a greenhouse, in a 13 cm pot. Age of the plant photographed is approximately 60 days from a rooted cutting.

Figure 2:
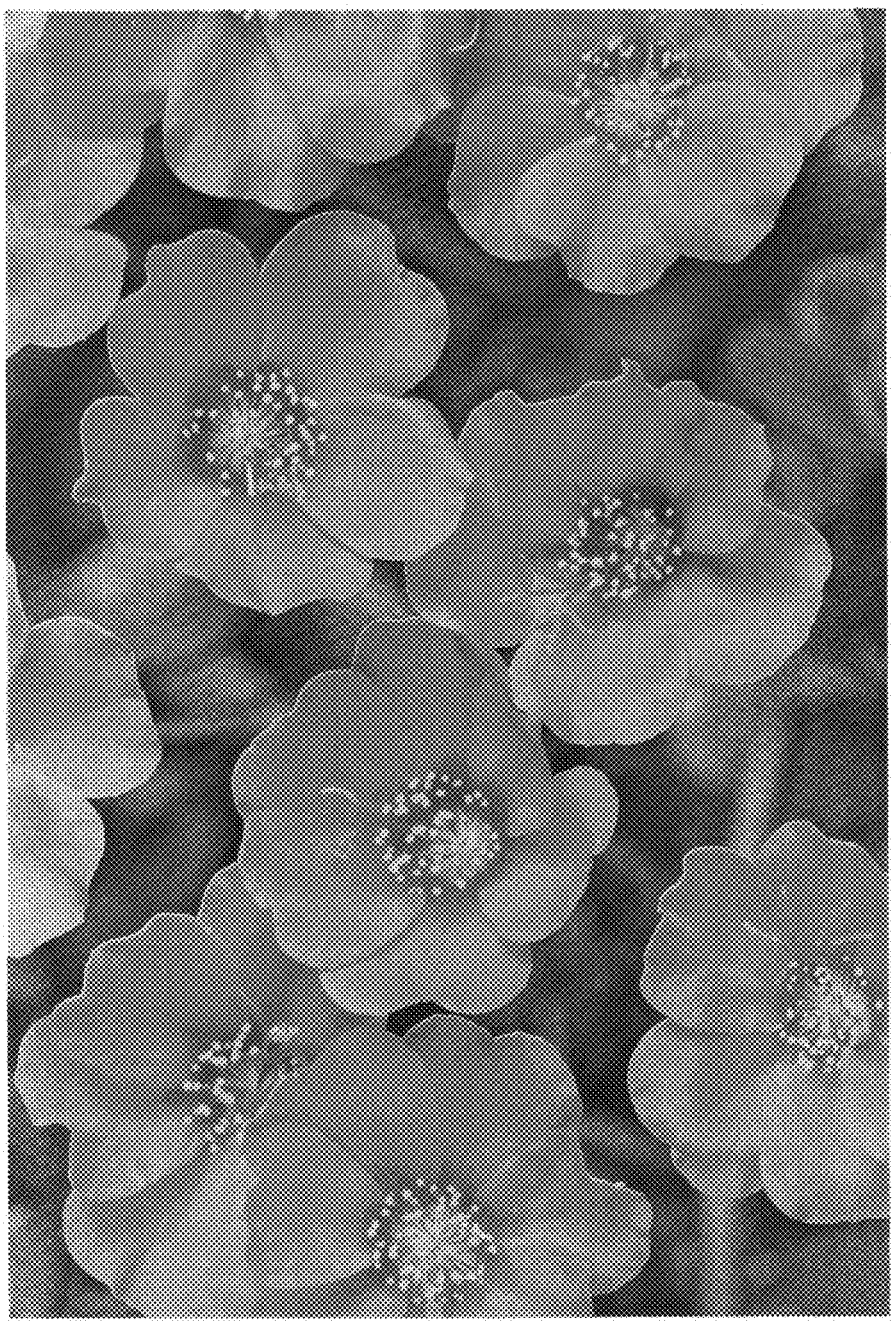

FIG. 2 illustrates a close up of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DPAZFCHSIA' plants grown in the October in a greenhouse, in Moshav Mishmar Hashiva, Israel. The growing temperature ranged from 14° C. to 30° C. during the day and from 10° C. to 23° C. during the night. General light conditions are bright, normal sunlight. Measurements and numerical values represent averages of typical plant types.

Botanical classification: *Portulaca oleracea* 'DPAZFCHSIA'.

PROPAGATION

Type of propagation typically used: Cutting.
Time to initiate roots: 10-14 days at approximately 18-21° C.
Root description: Fibrous, spreading and dense.

PLANT

Age of plant described: 60 days from a rooted cutting.
Container size of the plant described: 13 cm.
Growth habit: Semi-trailing.
Height: 17 cm.
Plant spread: About 28 cm (radius).
Growth rate: Medium vigor, semi-trailing growth habit.
Branching characteristics: Tight, compact, dense branching.
Length of primary lateral branches: 26 cm.
Diameter of lateral branches: 0.3-0.5 cm.
Quantity of primary lateral branches: About 8.
Characteristics of primary lateral branches:
- *Form*.—Horizontal. Rounded with ridges along the branch.
- *Diameter*.—Approximately 0.4 cm.
- *Color*.—From the base RHS Greyed-orange 176A-176B. From the tip RHS Yellow-green 144A.
- *Texture*.—Glabrous.
- *Strength*.—Flexible.

Internode length: Approximately 3 cm.

FOLIAGE

Leaf:
- *Arrangement*.—Alternate.
- *Quantity*.—Approximately 36 per branch.
- *Average length*.—3.5 cm.
- *Average width*.—1.4 cm.
- *Shape of blade*.—Oblanceolate.
- *Apex*.—Rounded tip in mature leaves and acute tips in younger leaves.
- *Base*.—Acuminate.
- *Margin*.—Entire.
- *Texture of top surface*.—Smooth.
- *Texture of bottom surface*.—Smooth.
- *Pubescence*.—Absent.
- *Aspect*.—Mainly flat, angle of attachment about 45°.
- *Color*.—Young foliage upper side: RHS Yellow-green 146A. Young foliage under side: RHS Yellow-green 146B. Mature foliage upper side: RHS Yellow-green 146A. Mature foliage under side: RHS Yellow-green 146B.
- *Venation*.—Indistinguishable from leaf blade.
- *Petiole*.—Absent.

FLOWER

Natural flowering season: Spring to Autumn in Moshav, Mishmar, Israel.
Days to flowering from rooted cutting: About 6 to 8 weeks.
Inflorescence and flower type and habit: Terminal inflorescence. Single flower. Flower held horizontal.
Rate of flower opening: 7 to 10 days from bud to fully opened flower.
Flower longevity on plant: Approximately 1 day.
Persistent or self-cleaning: Self cleaning.
Bud:
- *Shape*.—Narrowly conical.
- *Length*.—Approximately 0.8-1 cm.
- *Diameter*.—Approximately 0.5 cm.
- *Color*.—Bud base: RHS Yellow-green 144A with a purplish tip near RHS Red-purple 59A.

Flower size:
- *Diameter*.—3.2 cm.
- *Length*.—0.5 cm.

Corolla/petals:
- *Arrangement*.—Single flower with 5 distinct petals fused at base.
- *Length*.—Approximately 1.5 cm.
- *Width*.—Approximately 1.2 cm.
- *Quantity*.—5 petals.
- *Texture*.—Glabrous.
- *Apex*.—Rounded.
- *Shape*.—Obovate with a cuneate base.
- *Margin*.—Entire.
- *Color*.—When opening: Upper surface: RHS Red-purple N74B. Lower surface: RHS Red-purple 67C. Fully opened: Upper surface: RHS Red-purple N74B. Lower surface: RHS Red-purple 67C.

Calyx/sepals:
- *Quantity per flower*.—2 Sepals per flower.
- *Shape*.—Deltoid, elliptic with pointed tip.
- *Length*.—0.7 cm.
- *Width*.—0.5 cm.
- *Apex*.—Acute.
- *Base*.—Fused.
- *Margin*.—Entire.
- *Texture*.—Glabrous all surfaces.
- *Color*.—Upper Surface: RHS Yellow-green 144B bit purplish in the tip. Lower Surface: RHS Yellow-green 144B.

Peduncle: None.
Fragrance: No.

REPRODUCTIVE ORGANS

Stamens:
*Number*.—Many, around 60.
*Filament length*.—Approximately 0.2 cm.
Anthers:
*Shape*.—Oval, bilobed.
*Length*.—Less than 0.5 mm.
*Color*.—RHS Yellow-green 150D.
*Pollen*.—Color: Near RHS Orange N25B. Quantity: Many, around 60.
Pistil:
*Number*.—1 per flower.
*Length*.—0.7 cm.
*Style*.—Length: 0.5 cm. Color: Near RHS Yellow 2B.
*Stigma*.—Shape: Six branched stigma. Color: Near RHS Yellow-Orange 17A and pinkish in the center. Ovary Color: Near RHS Blue-Green 114B.

OTHER CHARACTERISTICS

Seeds and fruits: Fruits are egg-shaped 4 mm long with a conical shape top. Seeds are dark grey with a circular shape. Minute and not possible to correctly identify R.H.S. color.
Disease/pest resistance: No unusual susceptibility or resistance to diseases or insects has been observed.
Temperature tolerance: Will not tolerate temperatures below 7° C. High temperature tolerance to 40° C.

What is claimed is:

1. A new and distinct cultivar of *Portulaca* plant named 'DPAZFCHSIA' as herein illustrated and described.

* * * * *